United States Patent [19]

Hesse

[11] Patent Number: Plant 6,393

[45] Date of Patent: Nov. 15, 1988

[54] KALANCHOE PLANT NAMED LA CRUZ

[75] Inventor: Peter S. Hesse, Bradenton, Fla.

[73] Assignee: Ball Pan Am Plant Co., Parrish, Fla.

[21] Appl. No.: 6,135

[22] Filed: Jan. 23, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Kalanchoe plant named La Cruz characterized by its relatively large lavender to pink flowers, compact and free branching habit, early flowering, floriferous habit, and by its adaptability to production in 10 to 15 cm pots.

1 Drawing Sheet

The present invention relates to a new and distinctive cultivar of Kalanchoe plant, botanically known as Kalanchoe, and referred to by the cultivar name La Cruz.

The new cultivar was referred to during the breeding and selection process by the designation K82-402H-P and is a product of a planned breeding program. The basic objective of the breeding program was to create a new Kalanchoe cultivar having a large lavender-pink display of flowers, a freely breaking habit, early flowering response, and compact, vigorous growth habit.

La Cruz was originated from a cross made in a controlled breeding program in Parrish, Fla. The female, or seed parent was a cultivar designated Sensation (disclosed in U.S. Plant Pat. No. 4,727). The male, or pollen parent was the cultivar Red Star.

La Cruz was discovered and selected by me as a flowering plant within the progeny of the stated cross in a controlled environment in Parrish, Fla. Asexual reproduction of the new cultivar by stem cuttings, as performed by me at Parrish, Fla., has demonstrated that the combination of characteristics has herein disclosed for the new cultivar are firmly fixed and are retained through successive generations of asexual reproduction.

La Cruz has not been observed under all possible environmental conditions. The phenotype may vary significantly with variations in environment such as temperature, light intensity and day length. The following observations, measurements and values describe the new cultivar as grown in Parrish, Fla., under greenhouse conditions which closely approximate those generally used in commercial practice.

The following traits have been repeatedly observed and are determined to be basic characteristics of La Cruz, which in combination distinguish this Kalanchoe as a new and distinct cultivar:

1. Large lavender to deep pink flowers produced in abundance. Both lavender and pink are present at the same time, giving La Cruz a bicolor appearance.
2. Compact habit and average growth rate.
3. Freely branching, with shoots formed at every node.
4. Suitable for production in 10–15 cm pots, and flowering in 11–14 weeks using photoperiodic control.
5. Very floriferous, with numerous flowers formed at every node.
6. Responds to B-9 applications to control height.
7. Medium sized leaves which are very thick and persistent.

The new cultivar is most similar to Sensation. Chart A attached hereto compares certain characteristics of both cultivars. La Cruz is principally distinguished from Sensation by its lavender-pink flower color, two weeks earlier flowering response, and larger flower size.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under fluorescent light conditions in September in Parrish, Fla.

Botanical classification: Kalanchoe cv. La Cruz.

Parentage:

*Male parent.*—Red Star.

*Female parent.*—Sensation.

Propagation: The new cultivar holds its distinguishing characteristics through successive propagations by leaf cuttings and by division of shoots.

(A) *Type cutting.*—Shoot tip.

(B) *Time to root.*—Summer: 10–14 days at 21° C.

(C) *Rooting habit.*—Fibrous, many very fine roots.

Plant description:

(A) *Form.*—Upright, short, compact growth. Scheduling practices can produce small plants in 10 cm pots or large plants in 15 cm pots.

(B) *Habit of growth.*—Average for this type of plant; shoots are formed at every node.

(C) *Foliage description.*—Leaves simple, opposite, ovate with unevenly crenate margins. (1) Size: Up to 12 cm long and 7 cm wide. (2) Shape: Ovate. (3) Texture: Smooth, waxy and succulent. (4) Margin: Unevenly crenate. (5) Color: Young foliage top side 147B, under side 147B. Mature foliage top side 147A, under side, 14B.

Flowering description:

(A) *Flowering habit.*—Compound dichasial cyme on strong peduncles. Peduncle length depends upon growing conditions and B-9 applications. Pedicels up to 6 mm long.

(B) *Natural flowering season.*—Fall. Flowering time under controlled day length at 75°–85° F. in summer is 11–13 weeks; in winter at 62°–70° F., 11–13 weeks. Flowering time depends on temperature, light intensity and other growing conditions.

(C) *Flower buds.*—Oblong, developing to tubular as petals mature. Sheathed with four green sepals. Corolla at maturity about 12–14 mm long. (1) Size: Bud up to 12 mm long. (2) Shape: Oblong. (3) Rate of opening: Normal.

(D) *Flowers borne.*—Compound dichasial cyme on strong peduncles. Peduncle length depends on growing conditions and B-9 applications. Pedicles up to 6 mm long.

(E) *Quantity of flowers.*—Corolla funnel shaped, petal apex abruptly acuminate.

(F) *Petals.*—(1) Shape: Ovate with apex abruptly acuminate. (2) Color: Top side when opening, 64C and 52A, fading to 64D and 52B; under side, 52D. The application drawing clearly depicts the clearly distinguishable lavender and deep pink colors, which are present at various stages of maturity. (3) Number and size of petals: Four (4), petals 6–7 mm in diameter, total flower diameter 17 mm.

(G) *Reproductive organs.*—(1) Stamens: Eight (8) in number. (a) Anther shape: Flat elliptical. (b) Filament color: Yellow. (c) Pollen color: Yellow. (2) Pistels (a) Stigma shape: Flat, crystalline. (b) Style color: Greenish-white. (c) Ovaries: 4-celled, 7 mm long, green.

Disease resistance: No known Kalanchoe diseases observed to date.

General observations: La Cruz has large lavender and pink bicolored flowers, both of which are present at various stages of maturity. La Cruz has an early flower response and is very floriferous. La Cruz is adaptable to production in 10 or 15 cm pots years round.

CHART A

| | La Cruz vs. Sensation Summer Conditions | |
|---|---|---|
| | La Cruz | Sensation |
| Mature flower color | 64C and 52A | 58B (white eye) |
| Flowering plant height | 21 cm | 21 cm |
| Weeks to flower | 12 | 14 |
| Mature leaf width | 7 cm | 6 cm |
| Mature leaf length | 12 cm | 12 cm |
| Diameter of flower | 17 mm | 15 mm |

The plants of La Cruz and Sensation which were used in this comparison were grown together on the same bench in a greenhouse in Parrish, Fla. The color readings were taken under fluorescent light at 11:30 am on Sept. 24, 1986.

I claim:

1. A new and distinct cultivar of Kalanchoe plant named La Cruz, as described and illustrated, and particularly characterized by its relatively large lavender to pink flowers, compact and free branching habit, early flowering, floriferous habit, and by its adaptability to production in 10 to 15 cm pots.

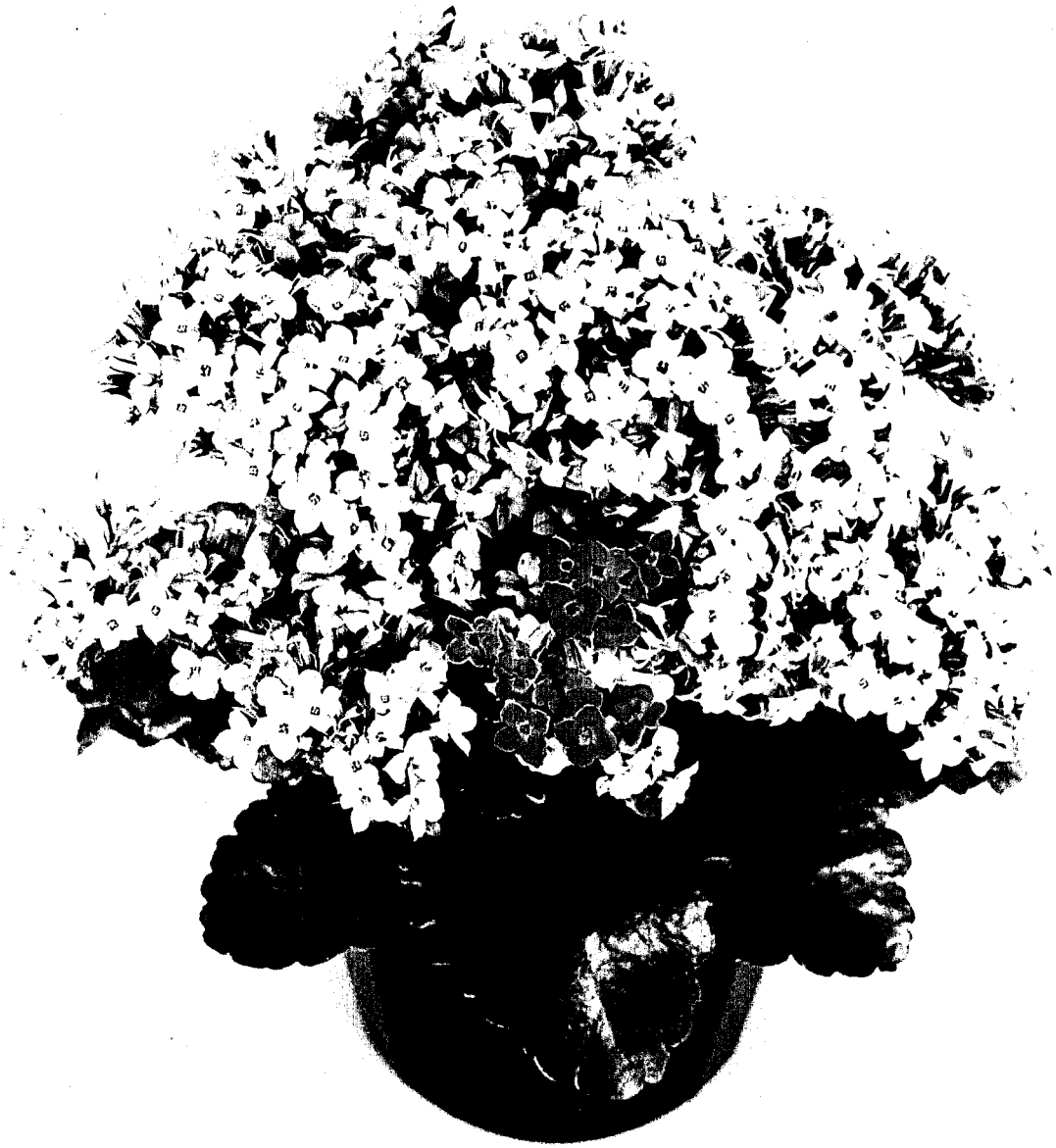

* * * * *